(12) United States Patent
Pardoel et al.

(10) Patent No.: US 8,688,230 B2
(45) Date of Patent: Apr. 1, 2014

(54) SYSTEM COMPRISING A BOX FOR IMPLANTING IN A BODY PART

(75) Inventors: Michel Gerardus Pardoel, Eindhoven (NL); Michel Marcel Jose Decre, Eindhoven (NL); Hubert Cécile François Martens, Eindhoven (NL); Franciscus Paulus Maria Budzelaar, Eindhoven (NL); Jozef Elisabeth Franciscus Gootzen, Eindhoven (NL); Jeroen Jacob Arnold Tol, Eindhoven (NL)

(73) Assignee: Sapiens Steering Brain Stimulation B.V. (NL)

( * ) Notice: Subject to any disclaimer, the term of this patent is extended or adjusted under 35 U.S.C. 154(b) by 112 days.

(21) Appl. No.: 13/265,408

(22) PCT Filed: Apr. 21, 2010

(86) PCT No.: PCT/IB2010/051741
§ 371 (c)(1),
(2), (4) Date: Nov. 17, 2011

(87) PCT Pub. No.: WO2010/122503
PCT Pub. Date: Oct. 28, 2010

(65) Prior Publication Data
US 2012/0059444 A1 Mar. 8, 2012

(30) Foreign Application Priority Data
Apr. 23, 2009 (EP) .................................. 09158638

(51) Int. Cl.
*A61N 1/08* (2006.01)
(52) U.S. Cl.
USPC ........................................................ 607/116
(58) Field of Classification Search
USPC ............................................ 607/2, 115–119
See application file for complete search history.

(56) References Cited

U.S. PATENT DOCUMENTS

| 5,796,254 | A | * | 8/1998 | Andrus ........................ 324/419 |
| 6,101,417 | A | * | 8/2000 | Vogel et al. ..................... 607/30 |
| 6,618,623 | B1 | | 9/2003 | Pless et al. |
| 6,741,892 | B1 | * | 5/2004 | Meadows et al. ............. 607/116 |
| 7,346,391 | B1 | | 3/2008 | Osorio et al. |
| 2003/0125786 | A1 | | 7/2003 | Gliner et al. |
| 2007/0225773 | A1 | | 9/2007 | Shen et al. |

OTHER PUBLICATIONS

International Preliminary Report on Patentability dated Nov. 3, 2011 for PCT/IB2010/051741.
International Search Report dated Sep. 23, 2010 for PCT/IB2010/051741.
Written Opinion dated Sep. 23, 2010 for PCT/IB2010/051741.

* cited by examiner

*Primary Examiner* — Brian T Gedeon
(74) *Attorney, Agent, or Firm* — Morgan, Lewis & Bockius LLP

(57) ABSTRACT

A system (102) comprising a box (104) for implanting in a mammal body part (106), which box is provided with a first electrical contact (110, 121, 114, 116, 118, 120), and a module (108) for accommodating in the box, which module is provided with a second electrical contact (122, 124, 126) for cooperation with said first electrical contact. The first electrical contact and the second electrical contact are mutually movable, at least in a stationary accommodation of the module in the box, between a contact position in which said first and second electrical contacts are electrically connected, and a non-contact position in which said first and second electrical contacts are separated from each other.

19 Claims, 2 Drawing Sheets

SYSTEM COMPRISING A BOX FOR IMPLANTING IN A BODY PART

Figure 1A:
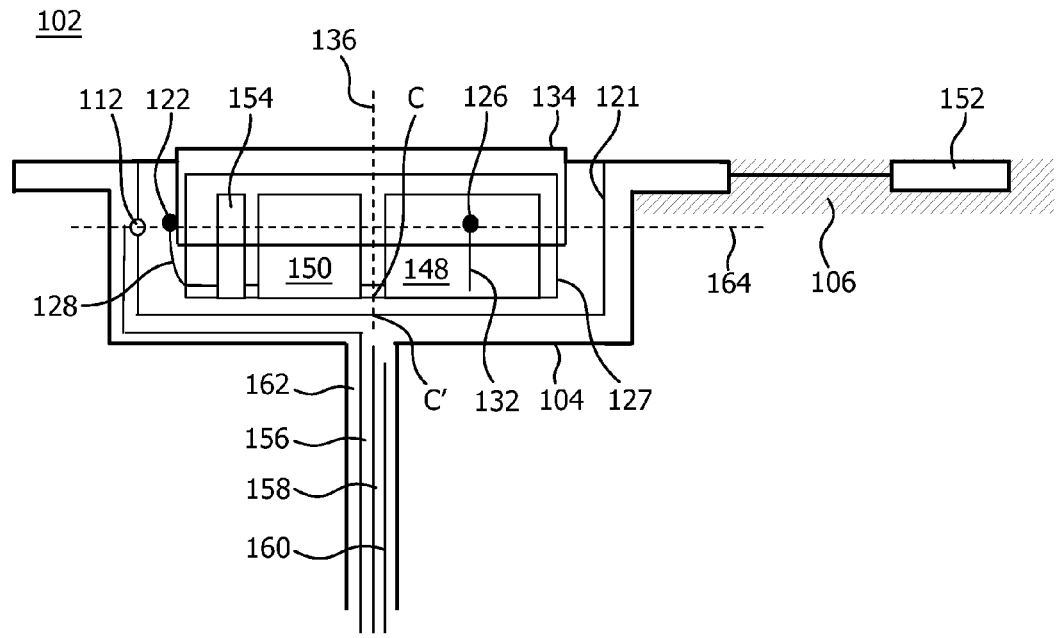

This application is a National Stage Patent Application of International Application No. PCT/IB2010/051741, filed Apr. 21, 2010, which claims priority to European Patent Application No. 09158638.8 filed on Apr. 23, 2009 which are each incorporated herein by reference in their entirety.

FIELD OF THE INVENTION

The invention relates to a system comprising a box implantable in a mammal body part and a module accommodatable in the box.

BACKGROUND OF THE INVENTION

In US-A 2007/0225773 A1, an implantable transcranial pulse generator for generating neuro-modulating electrical signals is disclosed. The generator according to US-A 2007/0225773 A1 comprises transcranial insert for mounting within a burr hole located in a skull of the patient, and a dome removably mounted to the transcranial insert. The dome and the insert contain electronic components and have complementary connectors facilitating direct electrical interconnection.

A disadvantage of the generator disclosed in US-A 2007/0225773 A1 is in the fact that mounting the dome to the transcranial insert exerts forces on said insert and will consequently load the burr hole in the patient's skull. Namely, a friction force present between the complementary connectors for facilitating direct electrical interconnection, has to be exceeded prior to mechanically joining the complementary connectors. This loading of the burr hole is undesired given a burr hole's vulnerable nature.

SUMMARY OF THE INVENTION

It is an object of the invention to provide a system of the kind defined in the opening paragraph, wherein forces exerted on the mammal body part during inserting the module into the box are reduced.

This object is achieved by the system according to the invention, which system comprises a box implantable in a mammal body part, which box is provided with a first electrical contact, and a module accommodatable in the box, which module is provided with a second electrical contact for cooperation with said first electrical contact, wherein the first electrical contact and the second electrical contact are mutually movable, at least in a stationary accommodation of the module in the box, between a contact position in which said first and second electrical contacts are electrically connected, and a non-contact position in which said first and second electrical contacts are separated from each other.

By enabling the first and second electrical contacts to be mutually movable between the contact and non-contact positions, at least in a stationary accommodation of the module in the box, no or practically no force will be exerted at the body part when inserting the module into the box with the purpose of accommodating the module in the box. Namely, by mutually moving the first and second contacts to the non-contact position prior to installing the module in the box, no friction will come into being between the first and second electrical contacts when inserting the module in the box and hence, no friction force between the first and second electrical contacts is to be exceeded in order to accommodate the module into the box. Consequently, in principle zero force will be exerted between the box and the module during an insertion of the module therein. As a result, presuming the module is implanted in the body part, a practically zero force will be exerted on said body part during inserting the module in the box.

The system according to the invention, and more specifically the box comprised in said system, is implantable in various mammal body parts. Nonetheless, an application of the system according to the invention will be specifically beneficial in mammal body parts having a vulnerable nature, such as a human skull. The box and the module are preferably manufactured from titanium or alloys of titanium with e.g. aluminum or vanadium.

In this document, an electrical contact is interpreted to be a discretely installed electrically conductive element, such as a pin, a prong or a flat surface. Hence, for instance, this document would consider a standardized CEE 7/17 plug, which is an unearthed alternating current (AC) power plug, to have two electrical contacts. Furthermore, this document likewise considers e.g. a standardized 8P8C modular connector plug to comprise eight electrical contacts. The first and second electrical contacts are manufactured from electricity conductive materials, preferably a phosphor bronze alloy or a platinum iridium alloy.

It is to be noted that a singular first electrical contact and a singular second electrical contact do suffice for establishing a circuit for a flow of a current. Namely, in applications driven by low-voltage current, typically a singular first electrical contact and a singular second electrical contact will be comprised in combination with a grounding element. It is stressed that at least parts of the box and the module comprised in the system may be implemented by electrically conductive materials, said parts establishing further electrical connections. In case said further electrical connections are made, a further path for current flow will be established. For instance, in case the box and the module are at least partially electrically conductive, they may establish said grounding element when brought into contact with one another. Typically, embodiments of the system according to invention will comprise a first set comprising at least two first electrical contacts, and a second set comprising at least two second electrical contacts, which first and second sets are mutually movable between a contact position in which the first and second sets are electrically connected and a non-contact position in which said first and second sets are separated from each other.

By accommodating the module in the box, a system's size is decreased compared to an architecture in which the module is not accommodatable in the box, which architecture must additionally comprise a cable comprising electrical wires for electrically connecting the module to the box. Consequently, the system according to the invention significantly reduces receiving a magnetic field imposed by a Magnetic Resonance Imaging (MRI) device, with that advantageously increasing MRI compatibility.

The absence of the cable for electrically connecting the box and the module in the system according to the invention is furthermore beneficial in that the patient no longer feels the annoying presence of the cable, which presence makes some patients start scratching their skin which may result in inflammations. Furthermore, installing the cable will take significant surgery time, which significant surgery time is prevented from by accommodating the module in the box.

In a preferred embodiment of the system according to the invention, the module is removable from the box in case the first and second electrical contacts are in the non-contact position. This embodiment has the advantage that it enables easily performing updates, revisions, replacements and/or repairs of the electronic circuit and the power source comprised in the module, which updates, revisions, replacements and/or repairs require a removal of the module with regard to the box. It is to be noted that the box is allowed to preserve its position with respect to the body part during said updates, revisions, replacements and/or repairs. The latter is highly beneficial advantageous given the fact that once the box is implanted in the body part, it will be connected to the soft tissue underneath the body part via an organically grown and rather fine mesh. The latter mesh, and the soft tissue surrounding the mesh, would be damaged by removing the box from the body part.

In a further practical embodiment of the system according to the invention, at least one of the first and second electrical contacts is resiliently deformable. This embodiment enables reliable way of mutually moving the first and second electrical contacts namely through resiliently deforming at least one of the first and second electrical contacts.

In a further preferred embodiment of the system according to the invention, the first and second electrical contacts are mutually mechanically stressable in the contact position. This embodiment has the advantage that a robustness of the contact position regarding disturbances affecting an electrical conductivity, such as manufacturing tolerances on the first and second electrical contacts and mechanical vibrations due to a patient's movement, is largely increased.

In a further preferred embodiment of the system according to the invention, the system is arranged for receiving an object, which object is configured for mutually moving the first and second electrical contacts between the contact position and the non-contact position through resiliently deforming at least one of the first and second electrical contacts. This embodiment has the advantage that it largely facilitates the medical professional in accommodating the module into the box. Namely, the object prevents the medical professional from having to resiliently deform at least one of the first and second electrical contacts him- or herself. Further, the object may perform as a handle for handling the module during accommodating the module into the box. Herein, the object is a creation having a specific geometry capable of resiliently deforming at least one of the first and second electrical contacts.

In a further preferred embodiment of the system according to the invention, the first and second electrical contacts are mutually mechanically stressable in the contact position by a presence of the object in the system. This embodiment has the advantage that it guarantees mechanical stressing of the first and second electrical contacts in the contact position, with that guaranteeing a certain level of robustness of the contact position regarding disturbances affecting an electrical conductivity, such as manufacturing tolerances on the first and second electrical contacts and mechanical vibrations due to a patient's movement.

In a further preferred embodiment of the system according to the invention, wherein the object is arranged for preventing the box from being closable by a cover in case the first and second electrical contacts are in the non-contact position. The cover is configured for hermetically sealing the box to prevent the box and the module from being polluted. This embodiment has the advantage it guarantees the first and second electrical contacts to be in the contact position once the box has been closed with the cover. The latter quality is beneficial in that it guarantees a therapy performable by the system, to be achieved indeed, which increases an effectiveness of the therapy. Furthermore, a patient's safety, which patient is dependent on said therapy, is largely improved. In addition to that, this embodiment of the system according to the invention prevents a patient from visiting a medical professional once again.

In a further preferred embodiment of the system according to the invention, the box and the module comprise cooperating key components for uniquely mounting the module in the box with regard to a mutual rotational degree of freedom for the box and the module around a common axis of rotation. This embodiment has the advantage that it prevents the module from being inaccurately installed in the box, with that preventing damage to both the module and box, especially damage to the first and second electrical contacts, and in that it reduces a period of time required to appropriately accommodate the box in the module. Generally, the key components are embodied by mutually complementary geometries, an example of mutually complementary geometries are mating cylinders and pin elements.

In a practical embodiment of the system according to the invention, the system is configured for electrically stimulating a brain. For this purpose, the module comprises an electronic circuit for generating a signal of electrical pulses and a power source for providing power to said electronic circuit, and the system comprises a probe incorporating an electrode for delivering said electrical pulses to the brain which electrode is electrically connected to the first electrical contact. In this particular embodiment, the box is preferably implanted in a skull encasing the brain.

In a further preferred embodiment of the system according to the invention, the probe is connected to the box. This embodiment has the advantage that it enables the probe to remain at its position inside the body part during a removal of the module with respect to the box. The latter is highly beneficial advantageous given the fact that once the probe is implanted in the body part, it will be connected to the soft tissue underneath the body part via an organically grown and rather fine mesh. The latter mesh, and the soft tissue surrounding the mesh, would be damaged by removing the probe from the body part.

In a further preferred embodiment of the system according to the invention, the power source comprises a rechargeable battery. This embodiment is advantageous in that it enables miniaturization of the power source compared to a further power source capable of providing equal power capacity but not suitable for recharging, with that reducing the system' size and thereby enhancing a patient's compliance with regard to the system's presence. Namely, when employing a non-rechargeable power source, a certain size will be required for it in order to guarantee an admissible lifespan.

In a further preferred embodiment of the system according to the invention, the system comprises an antenna for communicating, which antenna is connected to the box. This embodiment has the advantage that it allows the probe to remain at its position inside the body part during a removal of the module with respect to the box. The latter is highly beneficial advantageous given the fact that once the antenna is implanted in the body part, it will be connected to the soft tissue underneath the body part via an organically grown and rather fine mesh. The latter mesh, and the soft tissue surrounding the mesh, would be damaged by removing the antenna from the body part.

In a further practical embodiment of the system according to the invention, the antenna is arranged for wirelessly charging the rechargeable battery. Thereby the antenna offers a convenient way of charging the rechargeable battery.

In a further practical embodiment of the system according to the invention, the first contact is embodied by a contact area mounted on an interior of the box, and the second contact is mounted on an exterior of the module.

In a further preferred embodiment of the system according to the invention, the first electrical contact is part of a first set of first electrical contacts and the second electrical contact is part of a second set of second electrical contacts, wherein the first and second sets are mutually movable between a contact position in which said first and second sets are electrically connected, and a non-contact position in which said first and second sets are separated from each other, wherein the first set is installed in a first arrangement, wherein the second set is composed in a second arrangement, and wherein the first and second arrangements are rotationally symmetrical with respect to an axis perpendicular to Hertzian contact forces between the first and second electrical contacts in the contact position. This embodiment has the advantage that Hertzian contact forces exerted between the first and second electrical contacts will mutually cancel due to the rotationally symmetrical arrangements of first and second electrical contacts. Consequently, no other force will come into being in order to balance said Hertzian contact forces. In case the module is implanted in a mammal body part, no force other than the Hertzian contact forces will be exerted on the body part. As a result, a loading of said mammal body part is minimized. The latter is especially beneficial in case the module has been implanted in a vulnerable mammal body part, e.g. a human skull.

In this document, an arrangement is considered to be rotationally symmetrical with respect to an axis, in case there is at least one rotation of said arrangement with respect to said axis that results in a geometrically equal arrangement. The Hertzian contact force is the force caused by a stress that develops as mating parts are brought in contact with one another, and as a result of that, slightly deform. Herein, an amount of deformation is dependent on the mating parts' Young's Moduli of elasticity, their radii of curvature and the normal force between the mating parts.

In a further preferred embodiment of the system according to the invention, the system comprises at least three first contacts and at least three second electrical contacts. This embodiment has the advantage that an appropriate mutual positioning of the box and the module, i.e. a mutual positioning in which a geometrical center of the box is co-aligned with a geometrical center of the module in at least two dimensions, is automatically obtained. Namely, because of the rotationally symmetric arrangements of the at least three first and at least three second electrical contacts, the Hertzian forces exerted between the first and second electrical contacts in the contact position will cause the centers of the box and the module to be co-aligned in at least two dimensions. Preferably, the first and second electrical contacts are mutually mechanically stressed in the contact position.

In a further preferred embodiment of the system according to the invention, the box comprises at least two first electrical contacts and the module comprises at least two second electrical contacts for cooperation with the at least two first electrical contacts, wherein the probe incorporates at least two electrodes, and wherein the pulse generator is arranged for generating at least two signals of electrical pulses. This embodiment advantageously enables a spatially more refined therapy. Namely, by employing at least two electrodes, and by providing these at least two electrodes with an accompanying number of at least two signals of electrical pulses, which signals may be diversified, a spatially more refined pattern of signals of electrical pulses is deliverable to the brain.

In a further preferred embodiment of the system according to the invention, the number of the first electrical contacts is a multiple of the number of the second electrical contacts. This embodiment advantageously provides a degree of redundancy for the contact position with regard to the first electrical contacts. Namely, depending on a multiplicity of the number of the first electrical contacts compared to the number of the second electrical contacts, the contact position can be established by accommodating the module in the box in an according multiple number of ways. The latter quality has the advantage that in case of heavily polluted or damaged first electrical contacts, there is no need to remove the box from the body part, which removal is a lengthy procedure and is potentially dangerous due to its possible damaging effect on the tissue surrounding the box.

It is a further object of the invention to provide an object for use in the system according to the invention. This object is achieved by the object according to the invention. The object according to the invention is configured for mutually moving the first electrical contacts of the box and the second electrical contacts of the module between the contact position and the non-contact position. Herein the at least one of the first and second contacts is resiliently deformable. The object is arranged for resiliently deforming at least one of said first and second electrical contacts, at least in a stationary accommodation of the module in the box.

SHORT DESCRIPTION OF THE FIGURES

FIG. 1A schematically depicts a cross-sectional view of an embodiment of the system according to the invention, wherein the first and second electrical contacts are in the non-contact position.

Figure 1B:
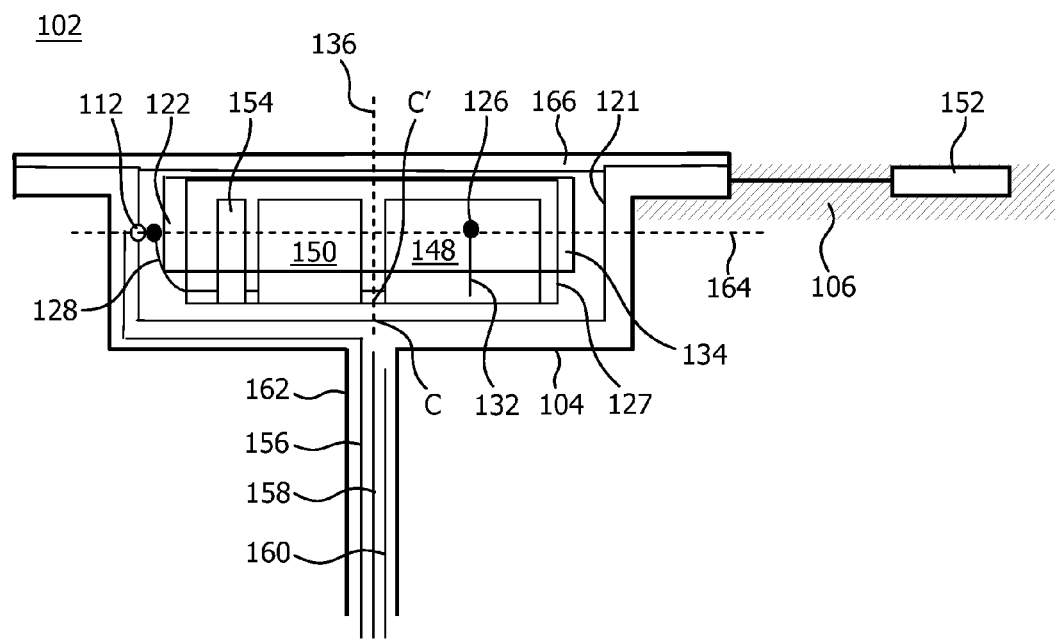

FIG. 1B schematically depicts a cross-sectional view of the embodiment depicted in FIG. 1A, wherein the first and second electrical contacts are in the contact position due to the presence of an object for resiliently deforming the second electrical contacts.

Figure 2A:
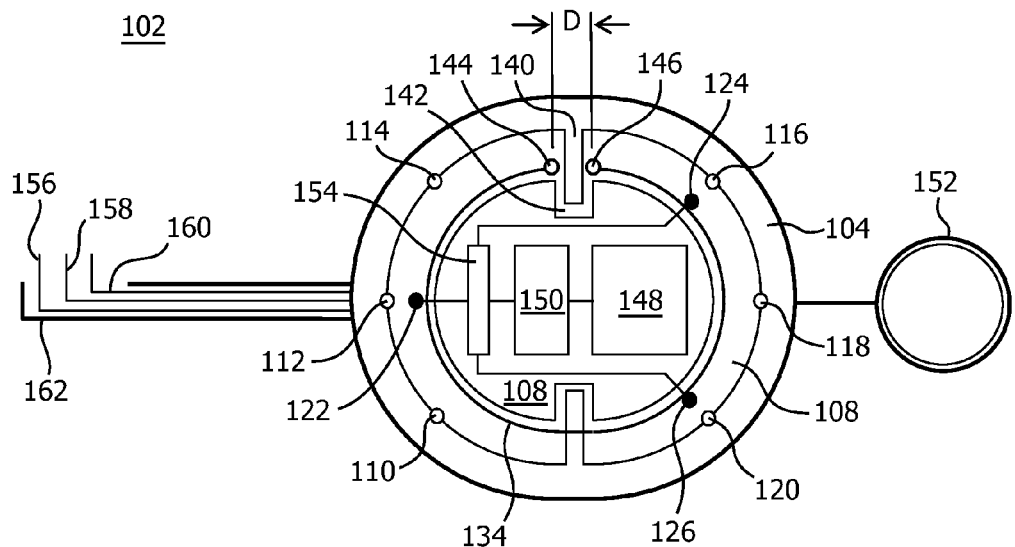

FIG. 2A schematically depicts a plan view of the embodiment depicted in FIG. 1A.

Figure 2B:
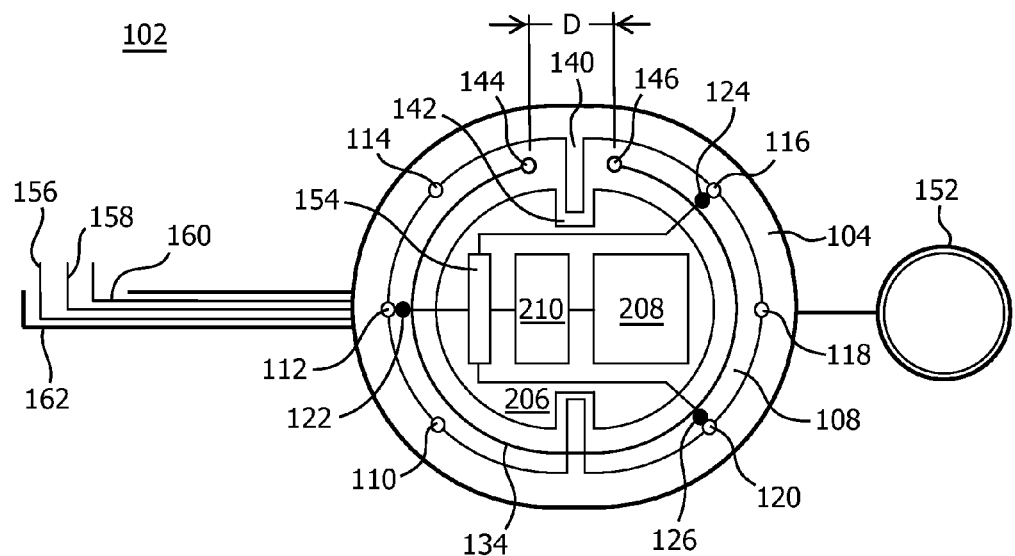

FIG. 2B schematically depicts a plan view of the embodiment depicted in FIG. 1B.

DETAILED DESCRIPTION OF THE EMBODIMENTS

FIG. 1A schematically displays a cross-sectional view of a system 102, which system is configured for electrically stimulating a brain. The system 102 comprises a box 104 for implanting in a body part 106, and a module 108 for accommodating in the box 104. In FIG. 1A, the module 108 is situated in a stationary accommodation in the box 104. Herein, the module is accommodated into the box along an axis 136, which axis 136 vertically passes through a geometrical center C of the module 108. In this example, both the box 104 and the module 108 are made from titanium, a.o. for its excellence resistance to corrosion. The box 102 is provided with a first set of electrical contacts comprising a first electrical contact 110 and first electrical contacts 112, 114, 116, 118 and 120, which are depicted in FIG. 2A.

Referring to FIG. 1A, the first electrical contacts 110, 112, 114, 116, 118 and 120 are mounted on an interior 121 of the box 104. Further, the first electrical contacts 110, 112, 114, 116, 118 and 120 are embodied by contact areas. The module 108 is provided with a second set of electrical contacts, comprising a second electrical contact 122 and second electrical contacts 124 and 126, which are shown in FIG. 2A, on its exterior 127. In this specific example, the number of first electrical contacts is a multiple of the number of second electrical contacts, with multiplicity two. The second electrical contacts 122, 124 and 126 are resiliently deformable. For that purpose the second electrical contacts 122, 124 and 126 comprise fiber-like elements 128, 130 and 132, respectively, which fiber-like elements 128, 130 and 132 allow for bending in a resilient manner. The latter degree of freedom is obtained by providing the fiber-like elements 128, 130 and 132 with a substantially small cross-sectional diameter compared to a length of the fiber-like elements 128, 130 and 132. In this example an object 134, which object is arranged for mutually moving the first and second sets of electrical contacts through resiliently deforming the second electrical contacts 122, 124 and 126, is removably mounted to the module 104. In this particular example, the object 134 is at least partially manufactured from an electrically isolating material such as a plastic. Namely, the object 134 is brought into contact with the fiber-like elements 128, 130 and 132 to which the second electrical contacts 122, 124 and 126 are being attached. Alternatively, the fiber like elements 128, 130 and 132 may be provided with an electrically isolating layer in order not to establish an electrical connection with the object 134.

Referring to FIG. 2A, a plan view of the system 102 is schematically depicted. The first electrical contacts 110, 112, 114, 116, 118 and 120 are arranged in a first arrangement, which first arrangement is rotationally symmetric with respect to the axis 136, see FIG. 1A Referring to FIG. 2A, the second electrical contacts 122, 124 and 126 are arranged in a second arrangement, which second arrangement is rotationally symmetric manner with respect to the axis 136. Furthermore, the second arrangement is concentrically arranged with regard to the first arrangement. In addition to that, the object 134 is concentrically situated with regard to the first and second arrangements. The box 104 and the module 108 are provided with cooperating key components 140 and 142, respectively. The key components 140 and 142 provide mutually complementary geometries. The key components enable an accommodation of the module 108 in the box 102 in which the second electrical contacts 122, 124 and 126 are positioned for cooperation with the first electrical contacts 110, 114 and 118, and a further accommodation wherein the second electrical contacts 122, 124 and 126 are situated for cooperation with the first electrical contacts 112, 116 and 120. Apparently, said further accommodation is obtainable by mutually rotating the box 104 and the module 108 along an angle of 180 degrees with respect to the axis 136. In order to keep the first and second electrical contacts in the non-contact position, the object 134 is to be retained in a mechanically stressed configuration by maintaining a sufficiently small distance D between an object's extremities 144 and 146. Said mechanically stressed configuration is accompanied by imposing a smaller radius of curvature for the object 134 compared to the radius of curvature pertaining to the object 134 in case no mechanical stress is introduced to it. For the purpose of maintaining the distance D between the object's extremities 144 and 146 sufficiently small, tools known per se are can be utilized by a medical professional.

Referring to FIG. 1B, through removing a constraint on the distance D, the set of second electrical contacts will be stressed by the object 134 and will consequently resiliently deform. A deformation of the second electrical contacts 122, 124 and 126 will be such that the first and second sets of electrical contacts will be situated in the contact position. Through mechanically stressing the object 134 once again, the sets of first and second contacts will be situated in the non-contact position, which enables the module 108 to be removably accommodatable in the box 104. Herein, the process of accommodating the module 108 into the box 104 and the process of removing the module 108 from the box 104, is largely facilitated through object 134. Namely, the object 134 performs like a handle, which handle assists the medical professional in handling the module 108 with regard to the box 104. The module 108 is removable from the box 104 along the direction established by the line 136.

Referring to FIG. 2B, in the contact position the first electrical contacts 112, 116 and 120 are electrically connected to the second electrical contacts 122, 124 and 126. The module 108 comprises a power source 148 for providing power to an electronic circuit 150, at least in operating conditions. In this example, the power source 148 is provided with a rechargeable battery, which rechargeable battery is wirelessly rechargeable through an antenna 152. That is, the antenna 152 is arranged for harvesting an energy comprised in an electromagnetic radiation directed towards the antenna 152, which energy is subsequently being fed to the battery, at least during operation. The antenna 152 is mounted to the box 104. The electronic circuit 150 is configured for generating three signals of electrical pulses. In operational conditions, said three signals are separated by a demuxer 154 prior to being distributed to the second electrical contacts 122, 124 and 126. By way of the first electrical contacts 112, 116 and 120, the signals of electrical pulses are forwarded to electrodes 156, 158 and 160, respectively. The electrodes 156, 158 and 160 are embedded within a probe 162. The probe 162 is mounted to the box 104 and is implantable in the body part 106 and more specifically, the brain underneath the skull. Via the probe 162, the electrodes 156, 158 and 160 deliver the signals of electrical pulses to the brain. In the contact position, the first electrical contacts 112, 116 and 120 and the second electrical contacts 122, 124 and 126 are mechanically stressed in cooperating pairs, i.e. the first electrical contact 112 and the second electrical contact 122 are mutually mechanically stressed and so on, by the object 134. For this purpose, a resistance of the object 134 regarding reducing its radius of curvature preferably significantly exceeds a resistance of the fiber-like elements regarding bending.

Referring to FIG. 1B, mechanically pre-stressing the first electrical contacts 112, 116 and 120 and the second electrical contacts 122, 124 and 126, results in Hertzian contact forces exerted between cooperating electrical contacts. Said Hertzian contacts forces are situated in a plane 164 perpendicular to the axis 136. Given the rotationally symmetrical first and second arrangements of electrical contacts, see FIG. 2B, the Hertzian contact forces will mutually cancel and no net force due to them will be exerted on the box 104. Furthermore, owing to the rotationally symmetrical first and second arrangements of electrical contacts, the geometrical center C of the module 108 will be co-aligned with a geometrical center C' of the box 104 in at least two dimensions.

While the invention has been illustrated and described in detail in the drawings and in the foregoing description, the illustrations and the description are to be considered illustrative or exemplary and not restrictive. For instance, instead of the second electrical contacts being resiliently deformable, the first electrical contacts may be implemented to be resiliently deformable. The invention is not limited to the disclosed embodiments. It is noted that the system according to the invention and all their components can be made by applying processes and materials known per se. In the set of claims and the description the word "comprising" does not exclude other elements and the indefinite article "a" or "an" does not exclude a plurality. Any reference signs in the claims should not be construed as limiting the scope. It is further noted that all possible combinations of features as defined in the set of claims are part of the invention.

The invention claimed is:

1. A system for electrical stimulation comprising:
   a box implantable in a mammal body part, the box being provided with a first electrical contact, and a module accommodatable in the box, the module being provided with a second electrical contact for cooperation with said first electrical contact,
   wherein the first electrical contact and the second electrical contact are mutually movable, at least in a stationary accommodation of the module in the box, between a contact position in which said first and second electrical contacts are electrically connected, and a non-contact position in which said first and second electrical contacts are separated from each other,
   wherein at least one of the first and second electrical contacts is resiliently deformable, and
   wherein the system is arranged for receiving an object, the object being configured for mutually moving the first and second electrical contacts between the contact position and the non-contact position through resiliently deforming at least one of the first and second electrical contacts.

2. The system according to claim 1, wherein the module is removable from the box in case the first and second electrical contacts are in the non-contact position.

3. The system according to claim 2, wherein the box comprises at least two first electrical contacts and the module comprises at least two second electrical contacts for cooperation with the at least two first electrical contacts, wherein a probe incorporates at least two electrodes, and wherein a pulse generator is arranged for generating at least two signals of electrical pulses.

4. The system according to claim 1, wherein the first and the second electrical contacts are mutually mechanically stressable in the contact position.

5. The system according to claim 1, wherein the first and second electrical contacts are mutually mechanically stressable in the contact position by a presence of the object in the system.

6. The system according to claim 1, wherein the object is arranged for preventing the box from being closable by a cover in case the first and second electrical contacts are in the non-contact position.

7. The system according to claim 1, wherein the box and the module comprise cooperating key components for uniquely mounting the module in the box with regard to a mutual rotational degree of freedom for the box and the module around a common axis of rotation.

8. The system according to claim 1, wherein the system is configured for electrically stimulating a brain, and wherein the module comprises an electronic circuit for generating a signal of electrical pulses and a power source for providing power to said electronic circuit, wherein the system comprises a probe incorporating an electrode for delivering said electrical pulses to the brain, wherein said electrode is electrically connected to the first electrical contact.

9. The system according to claim 8, wherein the probe is connected to the box.

10. The system according to claim 8, wherein the power source comprises a rechargeable battery.

11. The system according to claim 8 further comprising:
    an antenna for communicating, the antenna being connected to the box.

12. The system according to claim 11, wherein the antenna is arranged for wirelessly charging the rechargeable battery.

13. The system according to claim 1, wherein the first electrical contact is embodied by a contact area mounted on an interior of the box, and wherein the second electrical contact is mounted on an exterior of the module.

14. The system according to claim 1, wherein the first electrical contact is part of a first set of first electrical contacts and the second electrical contact is part of a second set of second electrical contacts, wherein the first and second sets are mutually movable between a contact position in which said first and second sets are electrically connected, and a non-contact position in which said first and second sets are separated from each other, wherein the first set is installed in a first arrangement, wherein the second set is composed in a second arrangement, and wherein the first and second arrangements are rotationally symmetrical with respect to an axis perpendicular to Hertzian contact forces between the first and second electrical contacts in the contact position.

15. The system according to claim 1 further comprising:
    at least three first contacts and at least three second electrical contacts.

16. The system according to claim 1, wherein the number of the first electrical contacts is a multiple of the number of the second electrical contacts.

17. A system for electrical stimulation comprising:
    a box implantable in a mammal body part, the box being provided with a first electrical contact, and a module accommodatable in the box, the module being provided with a second electrical contact for cooperation with said first electrical contact,
    wherein the first electrical contact and the second electrical contact are mutually movable, at least in a stationary accommodation of the module in the box, between a contact position in which said first and second electrical contacts are electrically connected, and a non-contact position in which said first and second electrical contacts are separated from each other,
    wherein the box and the module comprise cooperating key components for uniquely mounting the module in the box with regard to a mutual rotational degree of freedom for the box and the module around a common axis of rotation.

18. A system for electrical stimulation comprising:
    a box implantable in a mammal body part, the box being provided with a first electrical contact, and a module accommodatable in the box, the module being provided with a second electrical contact for cooperation with said first electrical contact,
    wherein the first electrical contact and the second electrical contact are mutually movable, at least in a stationary accommodation of the module in the box, between a contact position in which said first and second electrical contacts are electrically connected, and a non-contact position in which said first and second electrical contacts are separated from each other, and
    wherein the first electrical contact is part of a first set of first electrical contacts and the second electrical contact is part of a second set of second electrical contacts, wherein the first and second sets are mutually movable between a contact position in which said first and second sets are electrically connected, and a non-contact position in which said first and second sets are separated from each other, wherein the first set is installed in a first arrangement, wherein the second set is composed in a second arrangement, and wherein the first and second arrangements are rotationally symmetrical with respect to an axis perpendicular to Hertzian contact forces between the first and second electrical contacts in the contact position.

19. A system for electrical stimulation comprising:
- a box implantable in a mammal body part, the box being provided with a first electrical contact, and a module accommodatable in the box, the module being provided with a second electrical contact for cooperation with said first electrical contact;
- a probe having at least two electrodes; and
- a pulse generator configured to generate at least two signals of electrical pulses,
- wherein the first electrical contact and the second electrical contact are mutually movable, at least in a stationary accommodation of the module in the box, between a contact position in which said first and second electrical contacts are electrically connected, and a non-contact position in which said first and second electrical contacts are separated from each other,
- wherein the module is removable from the box in case the first and second electrical contacts are in the non-contact position, and
- wherein the box comprises at least two first electrical contacts and the module comprises at least two second electrical contacts for cooperation with the at least two first electrical contacts.

* * * * *